United States Patent
Majercak

(10) Patent No.: US 6,932,829 B2
(45) Date of Patent: Aug. 23, 2005

(54) CENTERING CATHETER

(75) Inventor: David C. Majercak, Stewartsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 71 days.

(21) Appl. No.: 10/178,434

(22) Filed: Jun. 24, 2002

(65) Prior Publication Data

US 2003/0236564 A1 Dec. 25, 2003

(51) Int. Cl.[7] .................................................. A61F 2/06
(52) U.S. Cl. ........................ 606/198; 623/1.11; 600/4
(58) Field of Search .............................. 623/1.11–1.15; 606/198; 604/96.01; 600/3

(56) References Cited

U.S. PATENT DOCUMENTS

| 5,421,832 A |   | 6/1995 | Lefebvre |
| 5,540,659 A | * | 7/1996 | Teirstein ..................... 604/104 |
| 5,910,101 A | * | 6/1999 | Andrews et al. ............... 600/3 |
| 6,210,312 B1 | * | 4/2001 | Nagy ............................ 600/3 |
| 6,213,976 B1 | * | 4/2001 | Trerotola ..................... 604/104 |
| 6,224,535 B1 | * | 5/2001 | Chiu et al. ..................... 600/3 |
| 6,267,775 B1 | * | 7/2001 | Clerc et al. .................. 606/198 |
| 6,280,414 B1 | * | 8/2001 | Shah et al. ................. 604/104 |
| 6,338,709 B1 | * | 1/2002 | Geoffrion et al. .............. 600/3 |
| 6,379,380 B1 | * | 4/2002 | Satz .......................... 623/1.15 |
| 6,450,988 B1 | * | 9/2002 | Bradshaw ................ 604/96.01 |
| 6,514,191 B1 | * | 2/2003 | Popowski et al. ............. 600/3 |
| 6,529,756 B1 | * | 3/2003 | Phan et al. ................. 600/374 |
| 6,533,753 B1 | * | 3/2003 | Haarstad et al. ......... 604/96.01 |
| 6,544,278 B1 | * | 4/2003 | Vrba et al. .................. 606/198 |
| 6,547,812 B1 | * | 4/2003 | Hu ............................. 623/1.11 |
| 2002/0010489 A1 |   | 1/2002 | Grayzel et al. |

* cited by examiner

*Primary Examiner*—David H. Willse
*Assistant Examiner*—Suzette J-J. Gherbi

(57) ABSTRACT

A catheter with at least one centering device attached near a distal end of the catheter. The centering device has at least two struts extending between a proximal end and a distal end. The centering device has a variable diameter and tends to center the distal end of the catheter, steering the catheter away from the vessel wall during insertion through the vasculature and toward the treatment site. The centering catheter may facilitate access to tortuous anatomy by preventing the catheter tip from catching on irregularities in the lumenal surface. The centering catheter may also facilitate uniform stent expansion by stabilizing the catheter during stent deployment.

11 Claims, 3 Drawing Sheets

CENTERING CATHETER

BACKGROUND AND SUMMARY OF THE INVENTION

1. Technical Background

The present invention relates to a catheter, and more particularly to a catheter with a centering tip.

2. Discussion

Percutaneous transluminal coronary angioplasty (PTCA) and stenting are therapeutic medical procedures used to increase blood flow through the coronary arteries and can often be used as alternatives to coronary bypass surgery. In PTCA procedures, the angioplasty balloon is inflated within the narrowed or stenosed vessel, at the desired location for treatment, such as an atheroma or plaque deposit, in order to obtain an enlarged opening or lumen. In stenting, an endoluminal prosthesis of any appropriate type is implanted in the vessel to maintain patency following the procedure. In order to initiate these procedures, one must first introduce a guidewire into the lumen of the vessel to serve as a conduit for other interventional devices, such as angioplasty balloons and stent delivery systems. This guidewire must be advanced into a position past the location of the stenosis. Additional interventional devices, such as angioplasty balloon catheters and stent delivery systems, are then advanced over the guidewire and positioned at the site of the stenosis, to initiate therapeutic treatment of the lesion.

A common treatment method for using such an angioplasty balloon catheter or stent delivery system is to advance the catheter into the body of a patient over the guidewire, by directing the catheter distal end percutaneously through an incision and along a body passage until the device is located within the desired site. One difficulty commonly encountered with the procedure is that irregularities of the lumenal surface and narrowing of the passageway may result in delivery difficulty, because the distal end of the balloon catheter or the stent delivery system may "catch" on the wall surface. This may cause a challenge in reaching the targeted position in the vessel, and therefore may inhibit successful treatment of the lesion. Another difficulty that is encountered with this procedure is that once the target lesion is reached, stent deployment may not be perfectly uniform if the stent delivery system is not centered within the vessel. This lack of centering may result in the stent cells around the circumference of the stent not opening up completely, resulting in non-uniform deployment. The end result may be reduced strength and incomplete stent scaffolding of the vessel, and a less than optimal clinical result.

The general concept of a centering catheter for treating a body vessel with a radioactive source is well known in the art. See, for example, U.S. Pat. Nos. 6,224,535 and 6,267,775.

However, the art has yet to disclose or suggest any devices for centering a non-radiation source catheter during its entire journey through the vasculature and to the treatment site, to facilitate access to tortuous anatomy, and then to promote uniform deployed stent expansion at the treatment site.

The present invention provides for a centering catheter which operates to remain centered during its entire journey through the vasculature and toward the treatment site, as well as at the treatment site, and which overcomes many of the disadvantages associated with the use and operation of prior art devices.

An objective of the present invention is to facilitate access to tortuous anatomy, so that a lesion location may be more easily reached and the vessel may be treated. Another objective of the present invention is to facilitate uniform deployed stent expansion by stabilizing the stent delivery system catheter and centering it in the vessel during stent deployment.

The centering catheter of the present invention comprises an elongated catheter body having a proximal end and a distal end, and at least one centering device attached near the distal end of the catheter. The centering device comprises a proximal end and a distal end and at least two struts extending therebetween. The centering device has a smaller diameter for insertion into a lumen and a larger diameter for expanding to substantially equal the diameter of the lumen and to center the catheter within the lumen. The centering device also has a plurality of intermediate diameters, between the smaller diameter and the larger diameter. These intermediate diameters may be utilized as the centering device adjusts to diameter variations in the lumen of the vessel during the catheter journey through the vasculature and toward the treatment site. Once the site is accessed, the centering device may also facilitate uniform stent delivery for either balloon expandable or self-expanding stents, by centering the distal end of the catheter during the deployment of the stent. Uniform stent expansion may contribute to a successful clinical outcome by insuring that optimal scaffolding of the vessel has occurred and optimal radial strength has been achieved to resist elastic recoil of the vessel following an interventional procedure. The catheter may then be withdrawn from the lumen of the vessel.

In accordance with one aspect, the present invention is directed to a catheter having at least one centering device attached near the distal end of the catheter. Each centering device comprises a proximal end and a distal end and at least two struts extending therebetween. Each centering device preferably has a variable diameter that centers the distal end of the catheter, steering the catheter away from the vessel wall during its insertion through the vasculature to the treatment site.

In accordance with another aspect, the present invention is directed to a stent delivery system comprising at least one centering device attached near the distal end of the stent delivery system. Each centering device comprises a proximal end and a distal end and at least two struts extending therebetween. Each centering device preferably has a variable diameter that centers the distal end of the catheter during the process of stent deployment.

An advantage of the present invention is that the sometimes-tortuous anatomy of the vasculature may be more easily traversed while avoiding lumen damage, and access to the lesion location may be facilitated by the availability of a centering device that centers the catheter throughout its introduction into the vessel. Another advantage of the present invention is that the centering device may stabilize the distal end of the catheter during stent expansion, and may therefore allow the operator to achieve a more uniform stent expansion with resultant clinical benefits to the patient.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE PREFERRED EMBODIMENTS

The centering catheter of the present invention is designed to facilitate access to a treatment site in a lumen of a vessel through tortuous anatomy, and to facilitate uniform stent deployment at the treatment site. The centering catheter of the present invention comprises an elongated catheter body having a proximal end and a distal end, and at least one centering device attached near the distal end of the catheter. The centering device comprises a proximal end and a distal end, and at least two struts extending therebetween. The centering device has a smaller first diameter for insertion into the lumen, a larger second diameter for expanding to substantially equal the diameter of the lumen of the vessel, and a plurality of intermediate diameters therebetween.

The centering device may be employed in any type of flexible elongated medical device product, including catheters, cannulae, guidewires and scopes. Although the centering catheter may be utilized in conjunction with any type of device, for ease of explanation, the exemplary embodiments described below will refer to a balloon catheter and stent delivery system.

Figure 1:
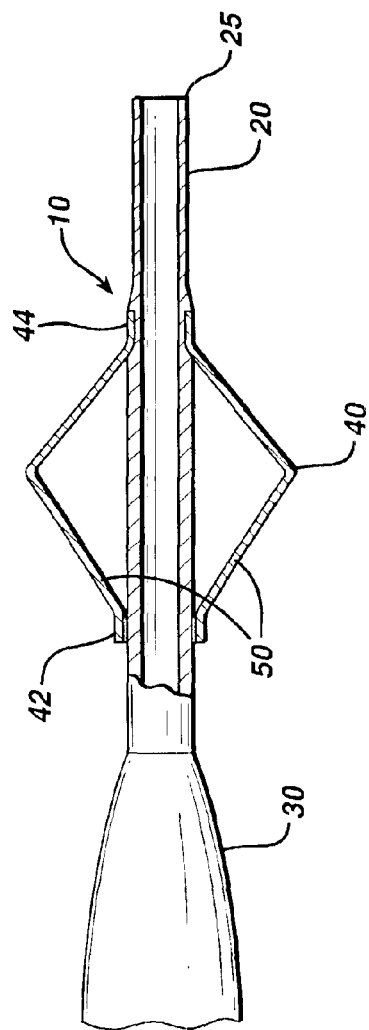
FIG. 1 is a diagrammatic, partial, enlarged, cross-sectional view of an example embodiment of the centering catheter, with the centering device on a balloon catheter, in accordance with the present invention.

While the present invention may be realized in a number of exemplary embodiments, for ease of explanation, two exemplary embodiments will be described in detail. Referring to the figures, there is illustrated in FIG. 1 a centering catheter 10 made in accordance with the present invention. The distal end of the centering catheter 10 comprises an inner member 20, which extends longitudinally through the centering catheter 10; a catheter tip 25; at least one centering device 40 attached to the circumference of the inner member 20; and an angioplasty balloon 30 attached to the inner member 20 proximal to the at least one centering device 40. Each centering device 40 comprises a proximal end 42 and a distal end 44 and at least two struts 50 extending therebetween. The struts 50 may be equally or unequally spaced. The struts 50 may be longitudinal, as illustrated in FIG. 1, or circumferential, or any number of other suitable configurations. As illustrated in FIG. 1, the centering device 40 has a larger diameter that substantially equals the diameter of the lumen, and substantially exceeds the diameter of the inner member 20. Therefore, the centering device 40 may center the tip 25 of the centering catheter 10 in the lumen during and throughout insertion into the vessel, until the treatment location is reached.

The at least one centering device 40 may be made from any number of suitable materials, and is preferably made from a superelastic alloy such as Nitinol. The struts 50 may alternatively be hingedly connected struts. The centering device 40 may be coated with any number of suitable materials, and is preferably coated with a lubricious or biologically compatible coating. The centering device 40 may be removably or permanently attached to the inner member 20. The centering catheter may be any suitable configuration catheter, and may preferably be an over the wire or rapid exchange catheter.

As illustrated in FIG. 1, the centering catheter may be advanced into the lumen of a vessel with the centering device 40 expanding to make contact with the walls of the lumen. The centering device 40 thus serves to center the distal end of the catheter 10 and its inner member 20 as it is pushed through the vasculature to the treatment site. The struts 50 are compressible and allow the centering device 40 to vary its diameter as the lumenal diameter varies, while always keeping the catheter tip 25 of the centering catheter 10 centered in the lumen. This may facilitate the pushability and trackability of the centering catheter 10 as it traverses the vasculature.

Figure 2:
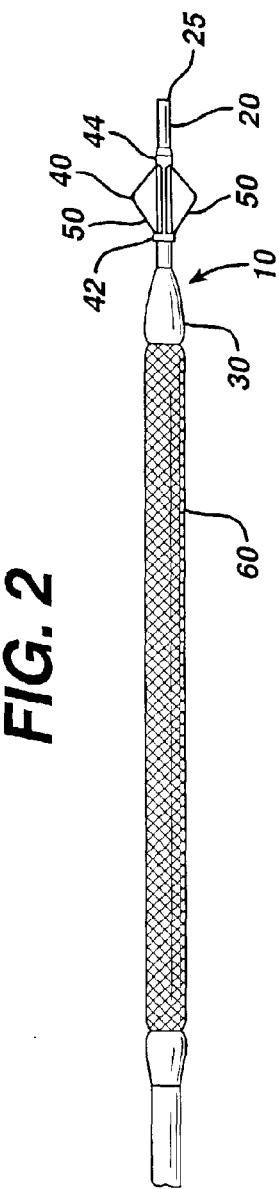
FIG. 2 is a diagrammatic, partial, enlarged, cross-sectional view of an example embodiment of the centering device, with the centering device on a stent delivery system, in accordance with the present invention.

FIG. 2 illustrates another exemplary made in accordance with the present invention. In this exemplary embodiment, a centering catheter 10 is a stent delivery system which comprises an inner member 20, which extends longitudinally through the catheter 10; a catheter tip 25; at least one centering device 40 attached to the circumference of the inner member 20; an angioplasty balloon 30 attached to the inner member 20 proximal to the at least one centering device 40; and a stent 60 mounted on the angioplasty balloon 30. Each centering device 40 comprises a proximal end 42 and a distal end 44 and at least two struts 50 extending therebetween. The struts 50 may be equally or unequally spaced. The struts 50 may be longitudinal, as illustrated in FIG. 2, or circumferential, or any number of other suitable configurations. As illustrated in FIG. 2, the centering device 40 has a larger diameter that substantially equals the diameter of the lumen, and substantially exceeds the diameter of the inner member 20. Therefore, the centering device 40 may center the catheter tip 25 of the centering catheter 10 in the lumen during and throughout insertion into the vessel, and during stent deployment. Another centering device may also be added to the centering catheter 10 at the proximal end of the stent 60 to facilitate uniform stent deployment.

The at least one centering device 40 may be made from any number of suitable materials, and is preferably made from a superelastic alloy such as Nitinol. The chronic outward force of the Nitinol may be increased, and/or the diameter of the centering device may be increased to enhance the stabilization of the system during stent deployment. The struts 50 may alternatively have hinges near their midpoints. The centering device 40 may also be coated with any number of suitable materials, and is preferably coated with a lubricious or biologically compatible coating. The centering device 40 may be removably or permanently attached to the inner member 20. The centering catheter 10 may be any suitable configuration catheter, and may preferably be an over the wire or rapid exchange catheter. The stent 60 may be a balloon expandable stent, as illustrated in FIG. 2, or a self-expanding stent.

As illustrated in FIG. 2, the centering catheter 10 may be a stent delivery system that is advanced into the lumen of a vessel, with the centering device 40 expanding to make contact with the walls of the lumen. The centering device 40 thus serves to center the distal end of the catheter 10 and its inner member 20 as it is pushed through the vasculature to the treatment site. The struts 50 are compressible and allow the centering device 40 to vary its diameter as the lumen diameter varies, while always keeping the catheter tip 25 of the centering catheter 10 centered in the lumen. This may facilitate the pushability and trackability of the centering catheter 10 as it traverses the vasculature. When the treatment site is reached, the centering device 40 may stabilize the stent delivery system in the lumen of the vessel to insure uniform stent 60 deployment.

Figure 3:
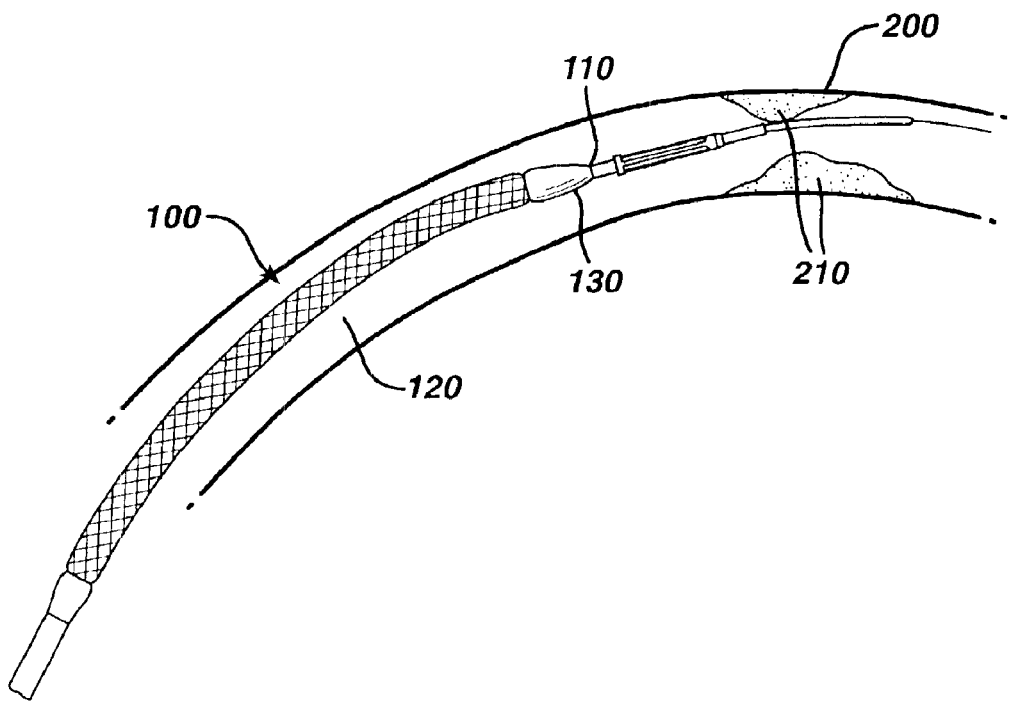
FIG. 3 is a diagrammatic, partial, enlarged, cross-sectional view of a non-centering stent delivery system catheter in an irregular and narrowed lumen of a tortuous vessel.

There is illustrated in FIG. 3 a non-centering catheter 100 in an irregular and narrowed lumen of a tortuous vessel 200. The lumen may be narrowed by plaques and other deposits 210 on the lumenal surface. The tip 110 of the non-centering catheter 100 may therefore become uncentered and may "catch" on the lumenal surface. Delivery of the noncentering catheter 110 to the targeted position in the lumen of the vessel may be difficult. In addition, deployment of a stent 120 (shown mounted on a balloon 130) may not be perfectly uniform.

Figure 4:
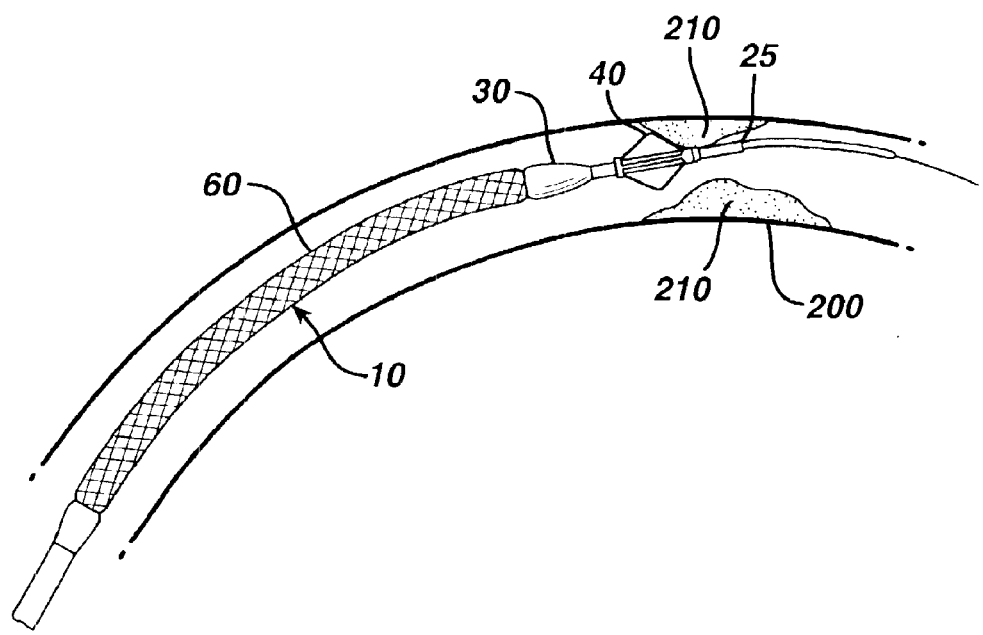
FIG. 4 is a diagrammatic, partial, enlarged, cross-sectional view of an example embodiment of the centering catheter, with the centering device on a stent delivery system in an irregular and narrowed lumen of a tortuous vessel, in accordance with the present invention.
Figure 5:
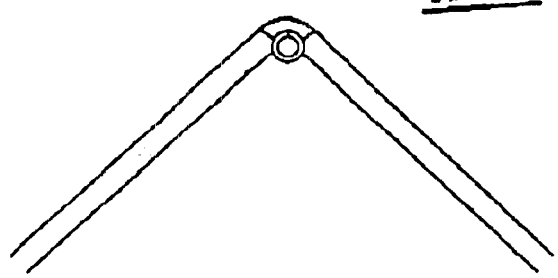
FIGS. 5—7 are partial views of struts having examples of hinges.
Figure 6:
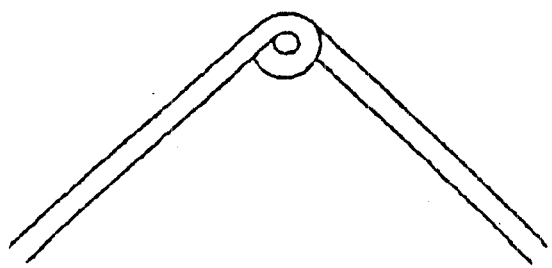
Figure 7:
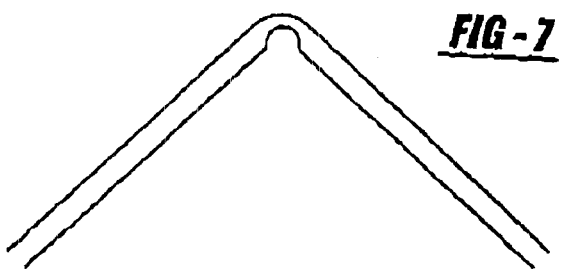

There is illustrated in FIG. 4 a centering catheter 10 with the at least one centering device 40 on a stent delivery system in an irregular and narrowed lumen of a tortuous vessel 200. The lumen may be narrowed by plaques and other deposits 210 on the lumenal surface. Delivery of the centering catheter 10 to the targeted position in the lumen of the vessel may be facilitated by the presence of the at least one centering device 40, which tends to center the tip of the catheter 25 in the lumen of the vessel 200. Deployment of a stent 60, shown mounted on a balloon 30, may be facilitated by the presence of the at least one centering device 40, which tends to center the catheter 10 within the vessel and facilitate uniform stent deployment.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cover all modifications that may fall within the scope of the appended claims.

What is claimed is:

1. A catheter for insertion into a lumen to treat a patient, the catheter comprising:

a) an elongated catheter body having a proximal end and a distal end, an outer dimension and an inner dimension; and b) at least one centering device attached near the distal end of the catheter, the at least one centering device comprising at least two struts extending between a proximal end c) and a distal end, the at least one centering device having a smaller first diameter for insertion into the lumen; a larger second diameter for expanding to substantially equal the diameter of the lumen, and to center the catheter in the lumen; and a plurality of intermediate diameters therebetween, wherein the at least two struts have midpoints, the at least two struts further comprising hinges near the midpoints.

2. The catheter according to claim 1, wherein the struts are made from Nickel-Titanium alloy.

3. The catheter according to claim 1, wherein the centering device is permanently or removably attached to the distal end of the catheter.

4. The catheter according to claim 1, wherein the catheter further comprises a balloon expandable stent.

5. The catheter according to claim 4, wherein the catheter further comprising a balloon expandable stent.

6. The catheter according to claim 4, further comprising a self-expanding stent.

7. The catheter according to claim 4, wherein the catheter further comprises a guidewire lumen in an over-the-wire configuration.

8. The catheter according to claim 4, wherein the catheter has multiple lumens.

9. The catheter according to claim 1, wherein the catheter further comprises a guidewire lumen in a rapid exchange configuration.

10. The catheter according to claim 1, wherein the struts are coated with a lubricious coating.

11. The catheter according to claim 1, wherein the struts are coated with a biologically compatible coating.

\* \* \* \* \*